United States Patent
Searfoss et al.

(10) Patent No.: US 12,226,628 B2
(45) Date of Patent: Feb. 18, 2025

(54) METHOD TO MANUFACTURE CUFF LEADS

(71) Applicant: Oscor Inc., Palm Harbor, FL (US)

(72) Inventors: Timothy Searfoss, New Port Richey, FL (US); Brian Walguarnery, Palm Harbor, FL (US); Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 565 days.

(21) Appl. No.: 17/534,004

(22) Filed: Nov. 23, 2021

(65) Prior Publication Data

US 2022/0184387 A1 Jun. 16, 2022

Related U.S. Application Data

(60) Provisional application No. 63/126,502, filed on Dec. 16, 2020.

(51) Int. Cl.
*A61N 1/00* (2006.01)
*A61N 1/05* (2006.01)

(52) U.S. Cl.
CPC .................. *A61N 1/0556* (2013.01)

(58) Field of Classification Search
CPC .................................. A61N 1/05446
See application file for complete search history.

(56) References Cited

U.S. PATENT DOCUMENTS

| | | | | |
|---|---|---|---|---|
| 4,059,890 A | * | 11/1977 | Sherwood | H05K 13/0007 29/760 |
| 4,602,624 A | * | 7/1986 | Naples | A61N 1/0556 607/118 |
| 4,686,765 A | * | 8/1987 | Byers | G09B 21/009 29/858 |
| 5,514,172 A | * | 5/1996 | Mueller | A61N 1/056 607/116 |
| 2006/0030919 A1 | * | 2/2006 | Mrva | A61N 1/0556 607/118 |
| 2008/0172116 A1 | * | 7/2008 | Mrva | A61N 1/0526 607/115 |
| 2011/0021943 A1 | * | 1/2011 | Lacour | A61N 1/0551 607/118 |
| 2011/0130818 A1 | * | 6/2011 | Chen | A61N 1/0539 427/430.1 |
| 2015/0138740 A1 | * | 5/2015 | Shin | C08L 83/04 522/182 |
| 2018/0126155 A1 | * | 5/2018 | McLaughlin | A61N 1/0558 |
| 2018/0333571 A1 | * | 11/2018 | Pepin | A61N 1/0556 |
| 2022/0355102 A1 | * | 11/2022 | Au | A61N 1/0556 |

FOREIGN PATENT DOCUMENTS

WO WO-2018111949 A1 * 6/2018 ........... A61B 5/0028

* cited by examiner

*Primary Examiner* — John R Downey
*Assistant Examiner* — Anant A Gupta
(74) *Attorney, Agent, or Firm* — Michael F. Scalise

(57) ABSTRACT

A method of manufacturing an implantable lead including a cuff is disclosed. The method includes partially curing a first silicone electrode cover, embedding electrodes within the first silicone electrode cover, partially curing a second silicone electrode cover, placing the first silicone electrode in a face-to-face relationship with the second silicone electrode cover to form an assembly, forming the assembly into a desired shape against a shim, placing an assembly within a canister to control an outer expansion, and curing the assembly.

20 Claims, 6 Drawing Sheets

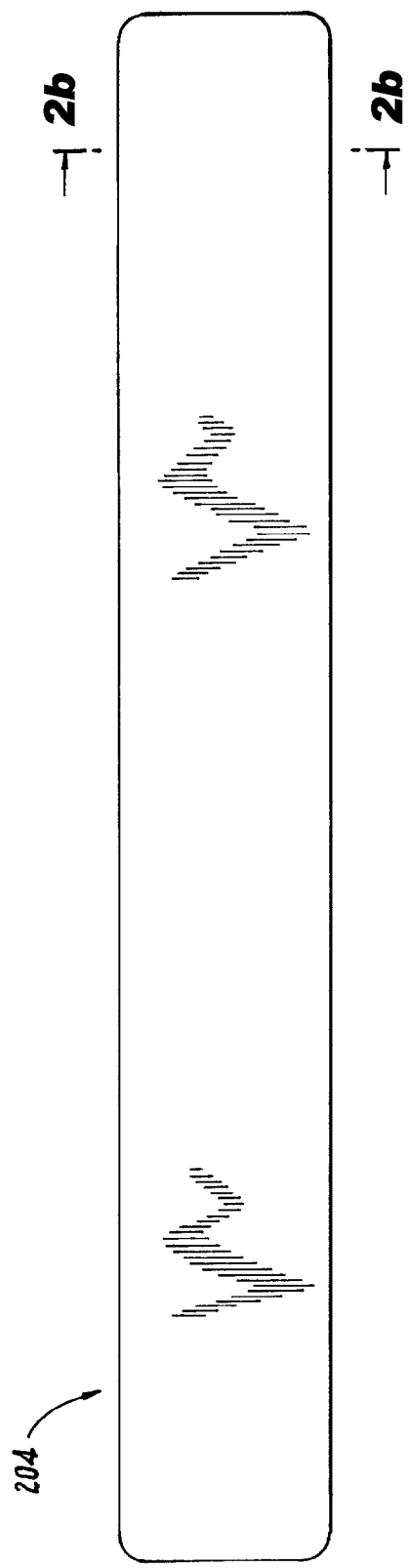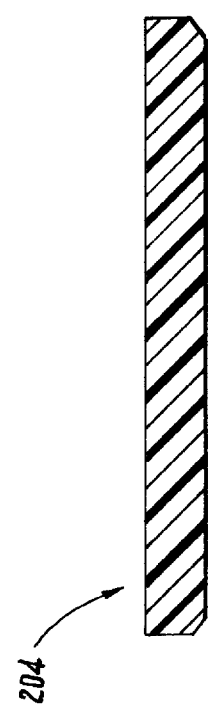
Fig. 2a
Fig. 2b

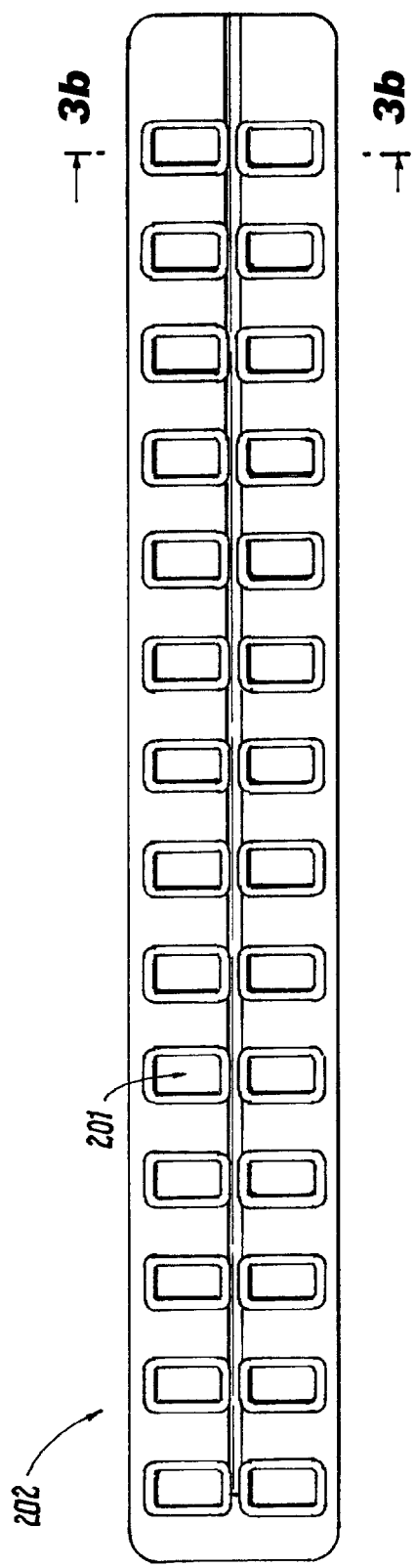
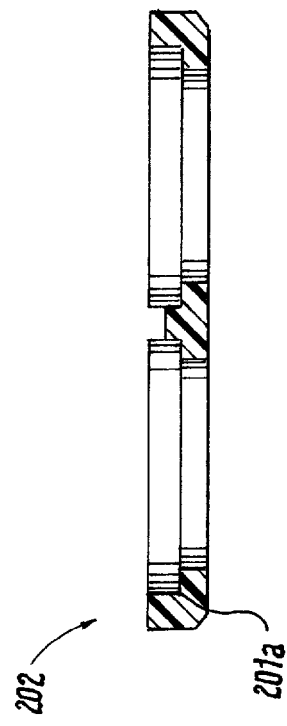
Fig. 3a
Fig. 3b

METHOD TO MANUFACTURE CUFF LEADS

CROSS-REFERENCE TO RELATED APPLICATION

The subject application claims the benefit of priority to U.S. Provisional Patent Application Ser. No. 63/126,502, which was filed on Dec. 16, 2020, the contents of which are incorporated by reference herein in their entirety.

BACKGROUND

Technological Field

The present disclosure relates to a method of manufacturing implantable cuff leads, and more particularly to a method of manufacturing implantable cuff leads used for electrical stimulation of nerves, muscles, veins or arteries.

Description of Related Art

Design and manufacture of implantable stimulation leads to be carefully wrapped around the nerves (e.g. Vagal nerve) or muscles or veins is standard practice in the area of neuro-modulation, cardiac-stimulation or other areas of the body where electrical signal using implantable devices to change electrical signals in nerves to treat a range of debilitating chronic diseases such as pain, incontinence, depression and diabetes. Similar application might include implantable neural probes for high-density recording for deep brain stimulation.

Typically such implantable leads are bipolar but can contain electrodes for multi-channel recording and stimulation, have an electrical insulated flexible lead body out of biocompatible and long term bio-stable material such as Polyurethane or Silicone, such lead body containing electrically insulated electrical conductors out of Pt/Ir, MP35N or DFT in either stranded wire or coil wound configuration, insulated against each other with either ETFE, PTFE or Polyimide, on the proximal end featuring a connector allowing the lead to be connected to an implantable stimulator, and on the distal end featuring a custom shaped electrode area in form of a custom shaped paddle or cuff. The distal cuff, which is in the clinical application implanted by the physician, and is carefully wound around a specific nerve, muscle, vein or artery needs to be soft enough to comply around the target nerve, muscle or artery, but strong enough to hold tight around the target area to allow effective stimulation. For that purpose, the distal cuff lead assembly is typically made of a compliant, biocompatible silicone material, such as platinum cured implantable grade silicone.

The manufacture of such distal cuff ends embedded with several stimulation electrodes can be quite challenging, in particular when the cuff shape is inner-wound in such a way, that a single or multi-step insert molding process is not plausible any more due to the shape constraints. Therefore, it is desirable to have a manufacturing process, which allows molding such cuff lead in the soft complaint Silicone material while forcing the cuff into shapes impossible to mold by liquid injection molding process. There is still a need in the art for manufacturing method allowing for greater shape complexity and material specificity. There also remains a need in the art for such methods that are economically viable. The present disclosure may provide a solution for at least one of these remaining challenges.

SUMMARY OF THE INVENTION

A method of manufacturing an implantable lead including a cuff is disclosed. The method includes partially curing a first silicone electrode cover, embedding electrodes within the first silicone electrode cover, partially curing a second silicone electrode cover, placing the first silicone electrode in a face-to-face relationship with the second silicone electrode cover to form an assembly, forming the assembly into a desired shape against a shim, placing an assembly within a canister to control an outer expansion, and curing the assembly.

The first silicone electrode cover and the second silicone electrode cover can include a platinum-cured elastomer. The partial curing can be between 2 and 15 seconds inclusive and between 120° and 180° Centigrade inclusive. Final curing can be between 120 and 240 minutes inclusive and above 180 degrees Centigrade inclusive. The method can include covering at least a portion of the embedded electrodes with a third semi-cured platinum-cured elastomer silicone cover. At least a portion of the embedded electrodes can be not covered by the at least one of the silicone covers.

The method can also include placing the first silicone cover or the second silicone against a shim in a face-to-face relationship. The desired shape can include at least one roll or coil, such as, at least 450-degree coil.

The method can also include flowing air over the assembly, between 80 and 110 liters per minute inclusive. The shim can include stainless steel or nitinol shims. The method can be used to a cuff adapted to be wound around a nerve including a first silicone layer defining a coil including a plurality of electrodes embedded within the silicone, a second silicone layer cured to the first silicone layer defining an assembly, a gap defining at least a partial space between the first silicone layer and the second silicone layer. The electrodes can be stamped platinum electrodes. The electrodes can be arranged in an array within the first silicone layer. A portion of each of the electrodes is uncovered. A portion of each of the electrodes can be flush with an outer surface of one of the covers.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein:

FIG. 2a is a top view of an uncured bottom cover of the cuff lead;

FIG. 2b is a side view of an uncured bottom cover of the cuff lead;

FIG. 3a is a top view of an uncured top cover of the cuff lead;

FIG. 3b is a side view of an uncured top cover of the cuff lead;

DETAILED DESCRIPTION

Figure 1:
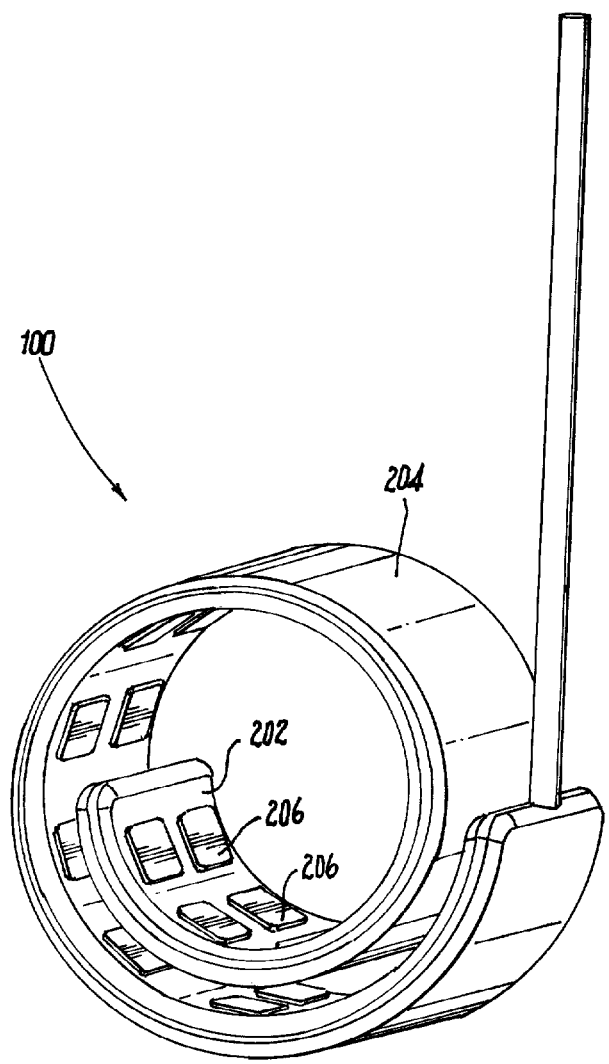
FIG. 1 is a perspective view of a cuff lead according to this disclosure.

Reference will now be made to the drawings wherein like reference numerals identify similar structural features or aspects of the subject invention. For purposes of explanation and illustration, and not limitation, a partial view of an exemplary embodiment of a cuff lead is shown in FIG. 1, which can be made using the manufacturing method shown in FIGS. 2-7. The methods and systems of the invention can be used to form a custom shaped implantable lead assembly.

FIG. 1 shows an implantable cuff lead 100. The cuff lead includes a top silicone electrode cover 202 and a bottom cover 204. Along with a plurality of electrodes 206 embedded therein. In order to produce an intricate shape as the one shown in the FIG. 1 a series of steps as shown in FIGS. 2-7 have to be performed.

Figure 4:
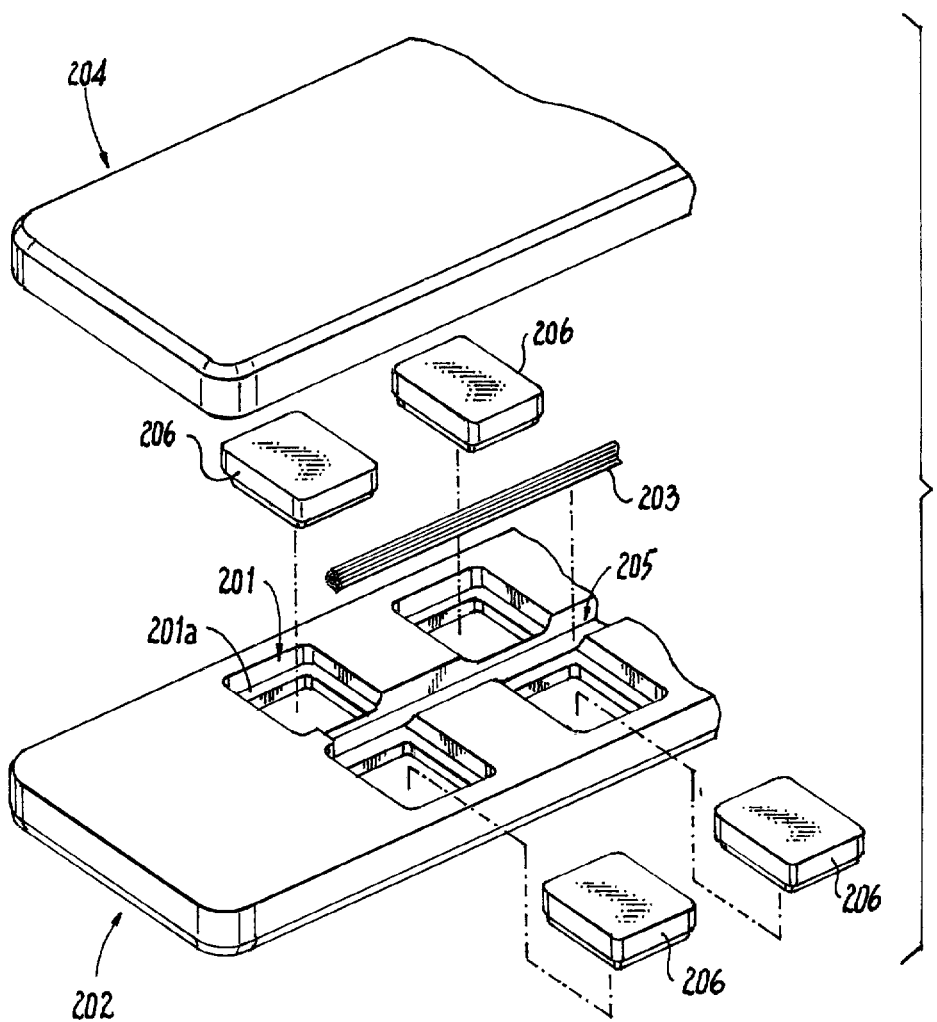
FIG. 4 is a perspective view of an assembly step of the cuff lead of FIG. 1, showing the placement of the electrodes.

FIG. 2a is a top view of an uncured bottom cover 204 of the cuff lead 100 and FIG. 2b is a side view of an uncured bottom cover 204. The bottom cover 204 can be flat in shape without electrode receptacles. FIG. 3a is a top view of an uncured top silicone electrode cover 202 of the cuff lead 100 and FIG. 3b is a side view of an uncured top silicone electrode cover 202. The top silicone electrode cover 202 can include a plurality of electrode receptacles 201. The receptacles can include a step 201a to ensure retention of the electrodes. Each of the covers 202/204 include a platinum-cured elastomer. Thermoplastics such as Pellethane or Polyurethane can also be used. The covers 202/204, originally, in liquid form are placed within molds. Each of the covers 202/204 are then partially cured. Afterwards each cover 202/204 is ejected from the mold as quickly as it can while still maintaining its shape. Partial curing requires between 2 and 15 seconds at a temperature between 120° and 180° Centigrade. Each of the covers 202/204 are set aside to cool to room temperature. After each of the covers 202/204 is partially cured, electrodes 206 are embedded into assembly 208 in an array within the top silicone electrode cover 202 as shown in FIG. 4. The electrodes 206 can be stamped platinum electrodes. Each of the electrodes 206 is connected to a wire 203, which is placed in a gap 205, by laser welding, resistance welding, or soldering.

Figure 5:
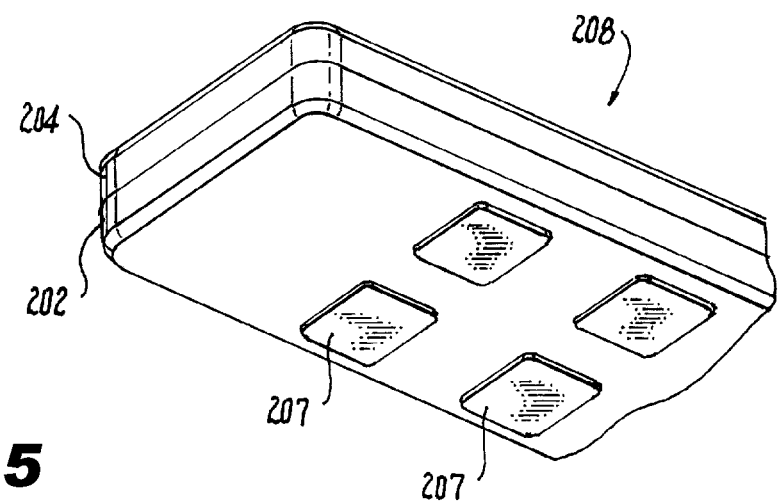
FIG. 5 is a perspective view of the partially cured top and bottom covers of FIG. 4, showing the implanted electrodes.

The bottom silicone electrode cover 204 is then placed on top of or in a face-to-face relationship with the top silicone electrode cover 202, covering up the electrodes 206 and forming an assembly 208 as shown in FIG. 5. A third semi-cured platinum-cured elastomer silicone cover can be used before the first and second covers are placed face-to-face in order to cover the electrodes. Some of the electrodes 206 can be left partially uncovered and expose a portion of the electrode 207 through the top cover 202.

Figure 6:
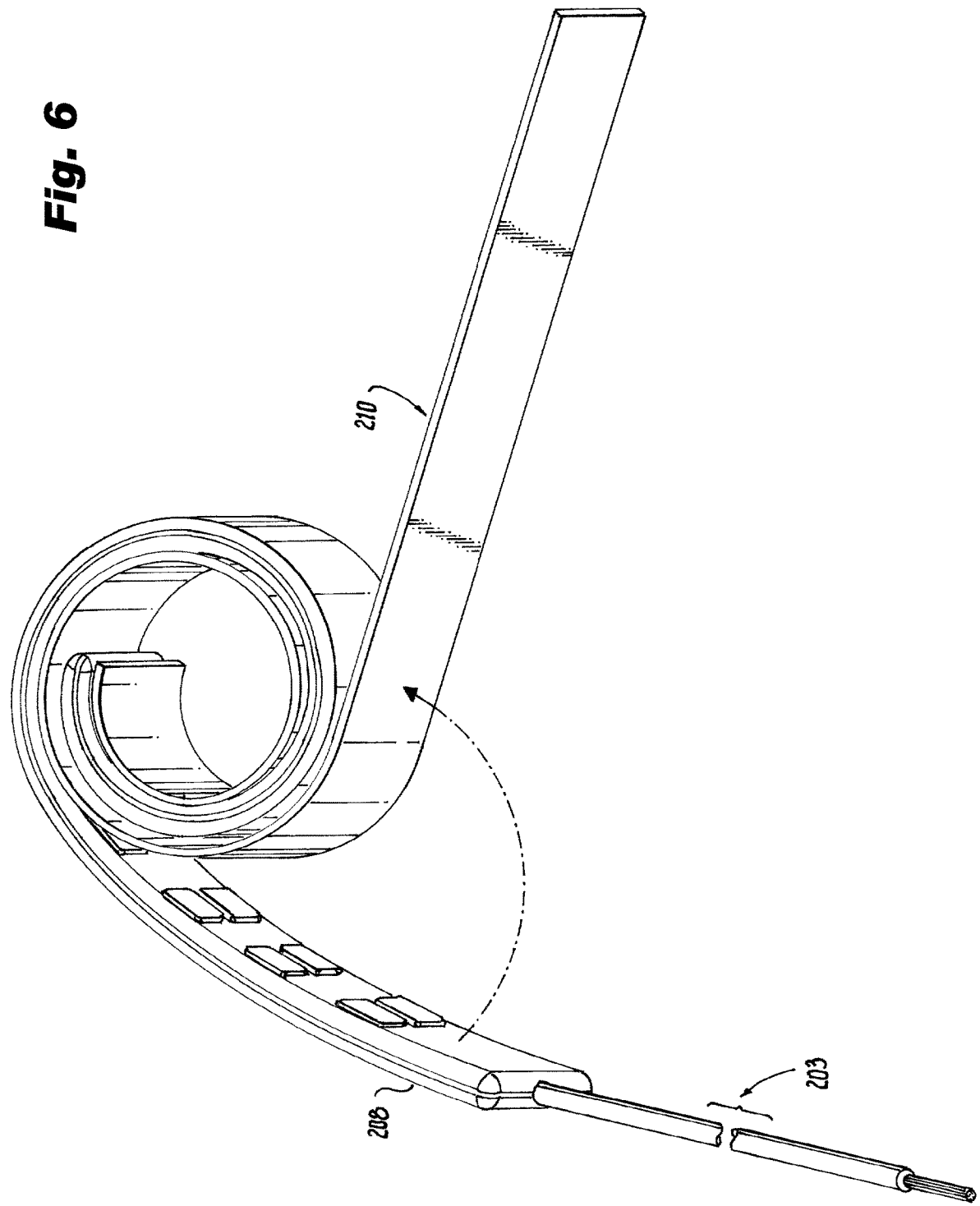
FIG. 6 is a perspective view of the partially cured top and bottom covers of FIG. 2, being coiled with the assembly of a shim.
Figure 7:
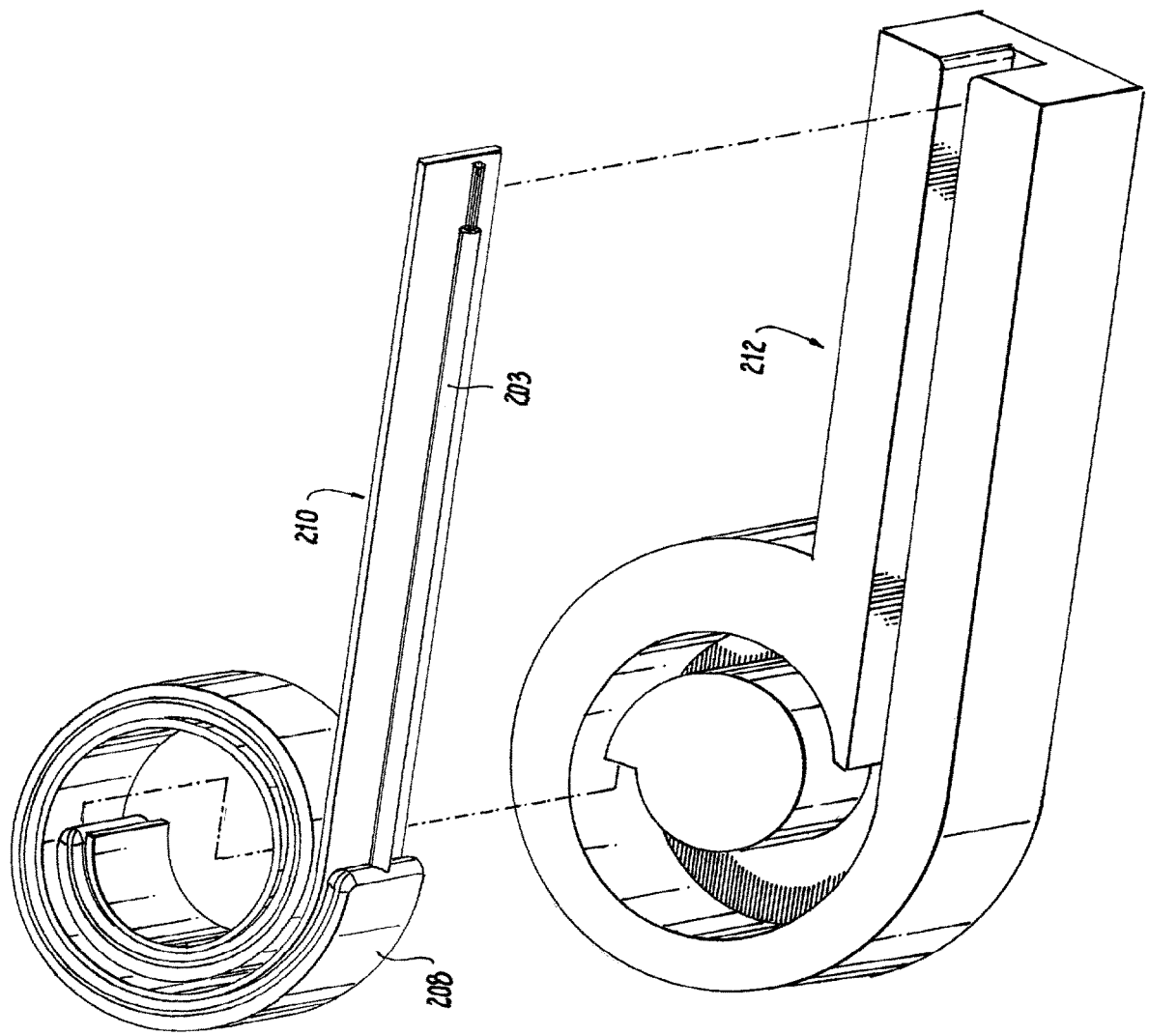
FIG. 7 is a perspective view of the partially cured top and bottom covers of FIG. 6, being inserted into a final curing mold.

The resultant assembly 208 is then placed against a flexible metal shim 210 and together with the shim 210, the assembly 208 carefully curled into a shape spanning more than 360 degrees where the electrode assembly is now in a spiral shape as shown in in FIG. 6. In FIG. 6 a coil is formed. In the particular case, the coil spans more than 450 degrees. The shim, which can be stainless steel or nitinol shim. The complete assembly 208 along with the shim 210 is then placed into an encasing canister 212, as shown in FIG. 7, that constrains the assembly to the desired outer diameter or thickness. The assembly 208, shim 210, and canister 212 are then placed into a curing oven. This oven is set with the appropriate curing temperature and airflow for the appropriate curing time according to the Liquid Silicone specification. The assembly 208 requires curing for 120 to 240 minutes at a temperature above 180 degrees Centigrade. The assembly 208 is then removed from the canister 212 when fully cured producing a final manufactured shape for implantable cuff leads, which can be used for electrical stimulation of nerves, muscles, veins or arteries.

The methods and systems of the present disclosure, as described above and shown in the drawings provide for a manufacturing method with superior properties including increased complexity. While the apparatus and methods of the subject disclosure have been showing and described with reference to embodiments, those skilled in the art will readily appreciate that changes and/or modifications may be made thereto without departing from the spirit and score of the subject disclosure.

What is claimed is:

1. A method for manufacturing an implantable lead, comprising the steps of:
    a) molding a top silicone layer having a thickness extending from a first surface to a second surface, wherein the molded top silicon layer has a plurality of electrode receptacles extending through its thickness and a gap extending from the second surface part-way through the thickness of the top silicone layer, the gap extending to an outer edge of the top silicone layer;
    b) embedding a plurality of electrodes in a respective one of the plurality of electrode receptacles in the top silicone layer so that an exposed electrode portion resides adjacent to the first surface of the top silicone layer, wherein each of the plurality of electrodes has a back surface that resides adjacent to the second surface of the top silicone layer;
    c) positioning a plurality of wires in the gap and connecting an electrode to a respective one of the plurality of wires;
    d) molding a bottom silicone layer;
    e) placing the bottom silicone layer on top of the second surface of the top silicone layer so that the bottom silicone layer covers the back surfaces of the plurality of electrodes and the plurality of wires in the gap in a face-to-face relationship with the top silicone layer to provide an assembly;
    f) forming the assembly into a desire shape against a shim;
    g) placing the assembly including the shim within a canister to control an outer expansion of the assembly; and
    h) curing the assembly in the canister.

2. The method of claim 1, including molding the top and bottom silicone layers comprising a platinum-cured elastomer.

3. The method of claim 1, including partially curing the top and bottom silicone layers for a period ranging from 2 seconds to 15 seconds inclusive before the steps of embedding the plurality of electrodes in a respective one of the plurality of electrode receptacles in the top silicone layer and positioning the plurality of wires in the gap.

4. The method of claim 1, including partially curing the top and bottom silicone layers at a temperature ranging from 120° Centigrade to 180° Centigrade inclusive before the steps of embedding the plurality of electrodes in a respective one of the plurality of electrode receptacles in the top silicone layer and positioning the plurality of wires in the gap.

5. The method of claim 1, including curing the assembly for a period that ranges from 120 minutes to 240 minutes inclusive.

6. The method of claim 1, including curing the assembly at a temperature that is above 180° Centigrade.

7. The method of claim 1, including providing each of the plurality of electrode receptacles having a step to ensure retention of the electrodes in their respective receptacle.

8. The method of claim 1, further including placing the first surface of the top silicone layer including the exposed electrode portions against the shim before curing the assembly.

9. The method of claim 1, including providing the desired shape for the assembly comprising at least one roll or coil.

10. The method of claim 9, including providing the desired shape for the assembly comprising a coil of greater than 360°.

11. The method of claim 1, including curing the assembly by flowing air over the assembly in the canister.

12. The method of claim 11, including providing the airflow ranging from 80 liters/minute to 110 liters/minute inclusive.

13. The method of claim 1, including removing the assembly including the shim from the canister when the assembly is fully cured.

14. The method of claim 1, including providing the shim as a stainless steel shim or a nitinol shim.

15. An implantable lead, comprising:
   a) a top silicone layer having a thickness extending from a first surface to a second surface, the top silicone layer having a plurality of electrode receptacles extending through its thickness and a gap extending from the second surface part-way through the thickness of the top silicone layer, the gap extending to an outer edge of the top silicone layer;
   b) a plurality of electrodes embedded in a respective one of the plurality of electrode receptacles of the top silicone layer so that an exposed electrode portion resides adjacent to the first surface and a back electrode portion of each of the plurality of electrodes resides adjacent to the second surface of the top silicone layer;
   c) a plurality of wires positioned in the gap of the top silicone layer, wherein one of the plurality of electrodes is connected to a respective one of the plurality of wires; and
   d) a bottom silicone layer cured to the second surface of the top silicone layer so that the bottom silicone layer covers the back surfaces of the plurality of electrodes and the plurality of wires in the gap in a face-to-face relationship with the top silicone layer to define an assembly.

16. The implantable lead of claim 15, wherein the plurality of electrodes are stamped platinum electrodes.

17. The implantable lead of claim 15, wherein the plurality of electrodes are arranged in an array within the top silicone layer, the array comprising at least two rows of paired side-by-side electrodes with the gap extending longitudinally between each of the paired electrodes, and wherein each of the electrodes is connected to a respective one of the plurality of wires.

18. The implantable lead of claim 15, wherein the exposed electrode portion of each of the plurality of electrodes is flush with or raised above the first surface of the top silicone layer.

19. The method of claim 1, including arranging the plurality of electrodes in an array within the top silicone layer, the array comprising at least two rows of paired side-by-side electrodes with the gap containing the plurality of wires extending Longitudinally between each of the paired electrodes, followed by connecting one of the electrodes to a respective one of the plurality of wires in the gap.

20. A method for manufacturing an implantable lead, comprising the steps of:
   a) molding a top silicone layer having a thickness extending from a first surface to a second surface, wherein the molded top silicon layer has a plurality of electrode receptacles extending through its thickness and a gap extending from the second surface part-way through the thickness of the top silicone layer, the gap extending to an outer edge of the top silicone layer;
   b) embedding a plurality of electrodes in a respective one of the plurality of electrode receptacles in the top silicone layer so that an exposed electrode portion resides adjacent to the first surface of the top silicone layer, wherein each of the plurality of electrodes has a back surface that resides adjacent to the second surface of the top silicone layer;
   c) positioning a plurality of wires in the gap and connecting one of the plurality of electrodes to a respective one of the plurality of wires;
   d) molding a semi-cured platinum-cured elastomer silicone layer;
   e) placing the semi-cured platinum-cured elastomer silicone layer on top of the second surface of the top silicone layer so that the semi-cured platinum-cured elastomer silicone layer covers the back surfaces of the plurality of electrodes and the plurality of wires in the gap in a face-to-face relationship with the top silicone layer;
   f) molding a bottom silicone layer;
   g) placing the bottom silicone layer on top of the semi-cured platinum-cured elastomer silicone layer to provide an assembly;
   h) forming the assembly into a desire shape against a shim;
   i) placing the assembly including the shim in a canister to control an outer expansion of the assembly; and
   j) curing the assembly in the canister.

* * * * *